United States Patent [19]
Jones et al.

[11] Patent Number: 5,452,611
[45] Date of Patent: Sep. 26, 1995

[54] ULTRASONIC LEVEL INSTRUMENT WITH DUAL FREQUENCY OPERATION

[75] Inventors: Lawrence Jones, West Dundee; Alexander J. Esin, Skokie; Boris S. Rosselson, Des Plaines, all of Ill.

[73] Assignee: Kay-Ray/Sensall, Inc., Mount Prospect, Ill.

[21] Appl. No.: 164,368

[22] Filed: Dec. 9, 1993

[51] Int. Cl.⁶ .................................................. G01F 23/28
[52] U.S. Cl. ........................ 73/290 V; 73/1 DV; 73/1 H
[58] Field of Search .................................. 73/1 H, 1 DV, 73/290 V; 324/76.49; 340/621, 521

[56] References Cited

U.S. PATENT DOCUMENTS

| | | | |
|---|---|---|---|
| 4,299,114 | 11/1981 | Silvermetz et al. | 73/1 H |
| 4,896,535 | 1/1990 | Duckart et al. | 73/290 V |
| 5,031,451 | 7/1991 | Webster | 340/621 |
| 5,155,472 | 10/1992 | Dam | 340/621 |
| 5,269,188 | 12/1993 | Esin | 73/1 DV |

FOREIGN PATENT DOCUMENTS

WO92/18835 10/1992 WIPO.

*Primary Examiner*—Robert Raevis
*Assistant Examiner*—Christine K. Oda
*Attorney, Agent, or Firm*—Westman, Champlin & Kelly

[57] ABSTRACT

An ultrasonic level instrument detects the presence of a fluid at a defined location and provides a self-diagnostic integrity check. An excitation circuit simultaneously induces vibrations at a first and second frequency in a transmitting piezoelectric crystal, and the vibrations are detected by a receiving crystal. A first and second filter circuit generate first and second filter outputs, respectively, by selectively passing the receiving crystal output at the first and second frequencies, respectively. The first filter output is indicative of the presence of fluid and the second filter output is indicative of the sensor integrity.

11 Claims, 3 Drawing Sheets

ULTRASONIC LEVEL INSTRUMENT WITH DUAL FREQUENCY OPERATION

BACKGROUND OF THE INVENTION

The present invention relates to ultrasonic devices that sense the presence of a material at a defined location. More particularly, the invention relates to a method and apparatus for monitoring the presence of such material at such defined location while also monitoring the integrity of the ultrasonic device itself.

In U.S. Pat. No. 4,299,114, Silvermetz et al. teach a method of testing the integrity of an ultrasonic system for sensing liquid-fluid interfaces. Transmit and receive crystals are disposed across a gap in a housing, and the output of the receive crystal feeds into an amplifier and bandpass filter network back to the transmit crystal. If the amplifier gain is high enough to overcome ultrasonic signal attenuation across the gap, then a selfsustaining oscillation results. Means is provided for shifting the bandpass filter network from a high to a low frequency passband. The high frequency passband is used for detection of the presence of fluid in the housing gap, and the low frequency passband is used for detection of system integrity. A feedback system of this type requires, for reliable operation, relatively stable liquid properties, and a relatively large difference between the amount of feedback with and without liquid present in the gap.

In U.S. Pat. No. 5,269,188, issued Dec. 14, 1993, entitled "Time Gate Ultrasonic Sensor and Method" and incorporated herein by reference, Esin et al. teach a device that monitors a received ultrasonic signal during a main time gate window to sense a property of a material in a defined space of the device housing. The device also monitors the received ultrasonic signal during a self-test time gate window to sense the integrity of the sensor. Both monitoring means receive the ultrasonic signal after the signal has been filtered by a single high pass filter. This device does not permit the use of different ultrasonic frequencies that are optimally tailored for the material property sensing and the integrity sensing functions.

BRIEF SUMMARY OF THE INVENTION

According to one aspect of the present invention, an ultrasonic level instrument includes transducer means for generating vibrations as a function of an electrical drive signal and for generating a transducer output as a function of received vibrations. An excitation circuit provides the electrical drive signal to induce the vibrations simultaneously at a first and second frequency. A first and second filter circuit receive the transducer output and selectively pass the first and second frequency component, respectively, of the transducer output, thereby generating a first and second filter output, respectively. A control unit couples to the first and second filter circuits and indicates the presence of a fluid of interest as a function of the first filter output and indicates the integrity of the sensor as a function of the second filter output.

DETAILED DESCRIPTION OF THE PREFERRED EMBODIMENTS

Figure 1:
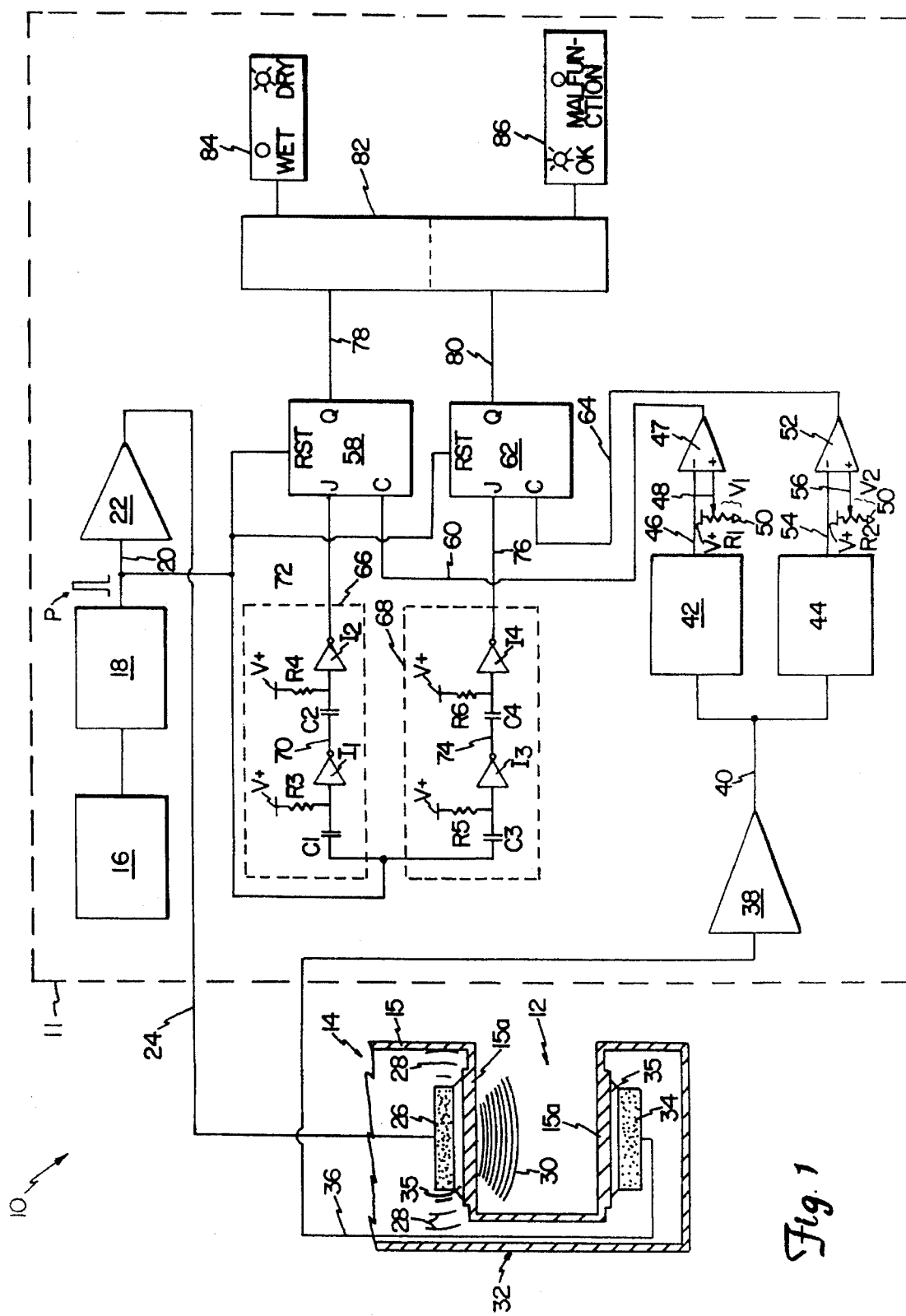
FIG. 1 is a representation of an ultrasonic device in accordance with the invention, including a partial cross-sectional view of an end of a sensor.

In FIG. 1, ultrasonic level instrument 10 comprises a sensor 14 and a controller 11. Instrument 10 senses the presence of a fluid, such as a liquid or other material, in a gap 12 at the tip of sensor 14. Typically, sensor 14 is a rod-shaped device mounted inside a tank in which the fluid is stored. Sensor 14 includes sensor housing 15 which contacts the fluid and isolates components interior to sensor 14 from contact with the fluid. Sensor housing 15 is preferably composed of metal, plastic, or other noncorrosive materials.

In controller 11, a cycle generator 16 periodically activates a pulse generator 18, which sends out a single pulse P over line 20 in response to each activation by cycle generator 16. Amplifier 22 receives pulse P and generates an amplified pulse, which excites a transmitting crystal 26 over line 24. Transmitting crystal 26, when so excited, vibrates simultaneously at two different ultrasonic frequencies, herein referred to as $f_{high}$ and $f_{low}$. The term "simultaneous" refers to at least some temporal overlap of the two vibrations. The duration of pulse P is approximately $1/(2*f_{high})$. Preferably, transmitting crystal 26 is selected such that it has a longitudinal frequency $f_{high}$ on the order of a few megahertz, for example about 1 MHz to 5 MHz. Vibrations at such high frequencies are advantageous for use in fluid detection because their attenuation through most fluids of interest is lower than through plastic or metal sensor housings. However, such vibrations are not preferred as indicators of sensor integrity because attenuation through plastic sensor housings is strongly affected by temperature, and further the attenuation can be significantly different among similar plastic pans. The diameter (or other transverse dimension) of transmitting crystal 26 is preferably selected such that $f_{low}$, has a value of about 40 KHz to 400 KHz, $f_{low}$, and $f_{high}$ preferably having a relative ratio of ten or more. It has been found that, unlike the high frequency vibrations, attenuation of the low frequency vibrations through plastic materials changes very little as a function of temperature and among similar plastic materials, such as the group of teflon-based plastic materials. Hence, it is particularly advantageous to utilize the low frequency vibrations as an indicator of the integrity of sensors that have plastic housings. Low and high frequency vibrations are depicted in FIG. 1 as reference numerals 28 and 30, respectively. Low frequency vibrations 28 result from radial vibrations of crystal 26, thereby emanating preferentially outward from the periphery of crystal 26 as shown in FIG. 1. High frequency vibrations 30 result from thickness vibrations of crystal 26, thereby emanating predominantly from the two opposed faces of crystal 26 (the upward-propagating high frequency vibrations are not shown). Both vibrations 28,30 are capable of propagating throughout sensor housing 15 (including bridge portion 32) and also through gap 12. Some of the vibrations reach a receiving crystal 34, disposed across gap 12 from transmitting crystal 26. Receiving crystal 34 is preferably identical to transmitting crystal 26. Both crystals 26,34 are composed of a piezoelectric material such as lead zirconate titanate (PZT), or, for high temperature applications, lead metaniobate. Epoxy layers 35,35 firmly bond crystals 26,34 to portions 15a, 15a of sensor housing 15 proximate gap 12. Portions 15a,15a are commonly referred to as "windows" by workers in the art. The thickness of each epoxy layer 35 and of each portion 15a is selected to substantially equal one-half of an ultrasonic vibration wavelength in the respective materials at the frequency $f_{high}$. This construction allows crystals 26,34 to efficiently communicate with gap 12 at the high frequency and protects the crystals from potentially harmful materials exterior to sensor 14.

Housing configurations different from that shown in FIG. 1 can be used with the invention. For example, the sensor can have a slot at one end, oriented parallel to a longitudinal axis of the sensor. Preferably, the transit time of ultrasonic vibrations from the transmit crystal to the receive crystal via the gap is significantly different from the transit time of ultrasonic vibrations via the sensor housing, to ensure that vibrations traversing the gap are and vibrations traversing the sensor housing are not received by the receive crystal simultaneously.

Vibrations which reach receiving crystal 34 induce electrical signals in crystal 34 representative of such received vibrations. Line 36 communicates the induced electrical signals from crystal 34 to a video frequency amplifier 38. Video amplifier 38 has a bandwidth that is wide enough so that the amplifier output on line 40 includes frequency components of the input signal on line 36 at both $f_{high}$ and $f_{low}$. According to the invention, the output at 40 couples, preferably but not necessarily simultaneously, to both filters 42 and 44. Filter 42 transmits the high frequency ($f_{high}$) component but not the low frequency ($f_{low}$) component of the signal at 40. Filter 44 transmits the low frequency component but not the high frequency component of the signal at 40. Filter 42 can comprise a high-pass filter with a cut-on frequency between $f_{low}$ and $f_{high}$, and filter 44 can comprise a low-pass filter with a cut-off frequency between $f_{low}$ and $f_{high}$. Alternately, filters 42,44 can comprise narrow bandpass filters centered respectively on $f_{high}$ and $f_{low}$, to reduce system noise. Filters 42,44 can also include amplification. Filters 42,44, and other electronic components depicted in FIG. 1, can be of the type known to workers skilled in the art. Filter 42 feeds its filtered output at 46 to comparator 47. The other input to comparator 47 is an adjustable DC voltage $V_1$, established by the position of sliding contact 48 on resistor $R_1$, which in turn connects to the positive supply voltage $V^+$ on one end and to ground potential 50 on the other end. In similar fashion, comparator 52 accepts the filtered output of filter 44 on line 54, and also adjustable DC voltage $V_2$, established by the position of sliding contact 56 on resistor $R_2$.

The output of filter 42, comprising high frequency components, is strongly affected by the presence of fluid in gap 12 because of the low attenuation of the high frequency vibrations propagating through gap 12 when fluid is present ("wet" condition) compared to when fluid is absent from gap 12 ("dry" condition). Thus, the amplitude of the signal on line 46 is substantially greater in the wet condition compared with the dry condition. Voltage $V_1$ is optimally set to a level below the maximum amplitude achieved by the output of filter 42 when wet, but above the maximum amplitude achieved when dry. At this setting of $V_1$ comparator 47 output fluctuates only for a wet condition at gap 12. Comparator 47 output connects to the clock input of JK flip-flop 58 over line 60. The K input to flip-flop 58, not shown, connects to $V^+$.

It has been observed that, both where sensor housing 15 is composed of metal and where it is composed of plastic, the relatively low frequency oscillations on the output of filter 44 are weakly affected by the presence of fluid in gap 12. Most of the low frequency signal from crystal 34 is due to ultrasonic vibrations traveling through housing 15 (including bridge 32) from transmitting crystal 26 to receiving crystal 34. Consequently, sensor failure caused by detachment of either crystal 26 or 34 from rigid contact with housing 15, or by cracks or other defects in bridge 32, will result in a marked decrease of low frequency (as well as high frequency) signals from crystal 34. It has been observed that materials such as plastics, including Teflon Polyfluorocarbon Resin (manufactured by Dupont Corp. and herein referred to as "PFA"), have attenuation characteristics at high frequencies ($f_{high}$) that change substantially as a function of temperature and from one type of plastic material to another. It has also been observed that those same plastic materials have thermally stable and repeatable attenuation characteristics at low frequencies ($f_{low}$). Ultrasonic instrument 10 therefore independently monitors low frequency signals from receiving crystal 34, via filter 44, as an indicator of system integrity, and high frequency signals from crystal 34, via filter 42, as an indicator of fluid presence. Monitoring of low frequency vibrations results in a more reliable indication of sensor integrity. Voltage $V_2$ is set to a level slightly below the expected low frequency amplitude output by filter 42, so that detachment of crystals 26 or 34, or similar malfunctions, will cause the low frequency amplitude to fall below $V_2$. The output of comparator 52 therefore oscillates only when the sensor is intact. Such oscillations are received at the clock input of JK flip-flop 62 over line 64.

Pulse P couples via line 20 to wet/dry time gate generator 66 and to self-test time gate generator 68. The combination of capacitor $C_1$, resistor $R_3$, and inverter $I_1$ as shown generate a normally "LO" signal on line 70, but generate a "HI" output for a period beginning at the downward transition of pulse P and continuing for a first time period dictated by $C_1$ and $R_3$. The transition of comparator $I_1$ from HI to LO initiates on line 72 a transition in the output of inverter $I_2$, and of wet/dry time gate generator 66, from a normally LO state to a HI state for a second time period dictated by $C_2$ and $R_4$. In this fashion wet/dry time gate generator 66 generates a "time gate" on line 72, defined as the time interval when the generator output is HI. Self-test time gate generator 68 operates in like fashion, and includes capacitors $C_3$ and $C_4$, resistors $R_5$ and $R_6$, and inverters $I_3$ and $I_4$, connected as shown. The output of inverter $I_3$ on line 74 feeds into inverter $I_4$ through capacitor $C_4$, and the output of inverter $I_4$ yields a self-test time gate output on line 76. Time gate outputs at 72,76 are provided to the J input of JK flip-flops 58,62, respectively. The outputs of JK flip-flops 58,62 at Q are reset to LO by operation of pulse P along line 20 to the reset ("RST") inputs of flip-flops 58,62.

If desired, the logic function performed by JK flip-flops 58,62 can be performed by NAND gates or other digital components. However, use of JK flip-flops reduces the number of components needed for controller 11, thereby simplifying the controller and increasing instrument reliability.

The outputs of JK flip-flops 58,62 are provided to control unit 82 along lines 78,80, respectively. Control unit 82 can include counters or other known circuitry to monitor outputs 78,80 so as to ascertain the presence or absence of fluid in gap 12 and also to ascertain the integrity of sensor 14. For example, control unit 82 can include a counting circuit coupled to line 78 that indicates a dry condition on indicator 84 unless it counts 3 or more pulses on line 78 for each initialization pulse P, in which case such counting circuitry indicates a wet condition on indicator 84. Similar counting circuitry can monitor the signal on line 80 to indicate the integrity of the sensor at indicator 86, so that indicator 86 indicates a malfunction in sensor 14 unless a programmed number of pulses are detected on line 80 between successive pulses P. Preferably, control unit 82 activates indicators 84,86 independently of the signals on lines 80,78, respectively. Control unit 82 can also include current sources and relay drivers that are responsive to the presence of fluid at gap 12 and to the integrity of sensor 14.

Figure 2:
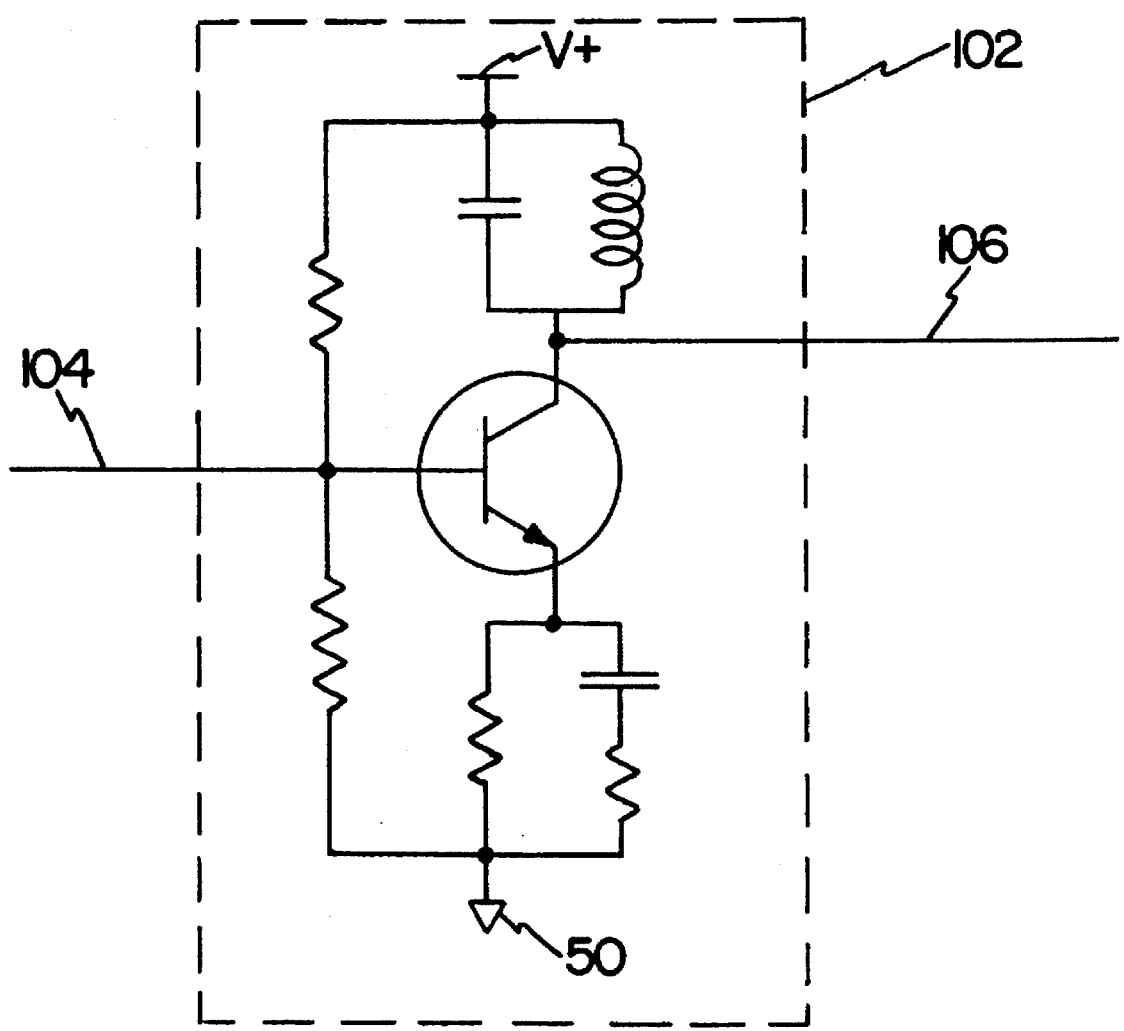
FIG. 2 is a schematic diagram of a filter circuit useable with the invention.
Figure 3:
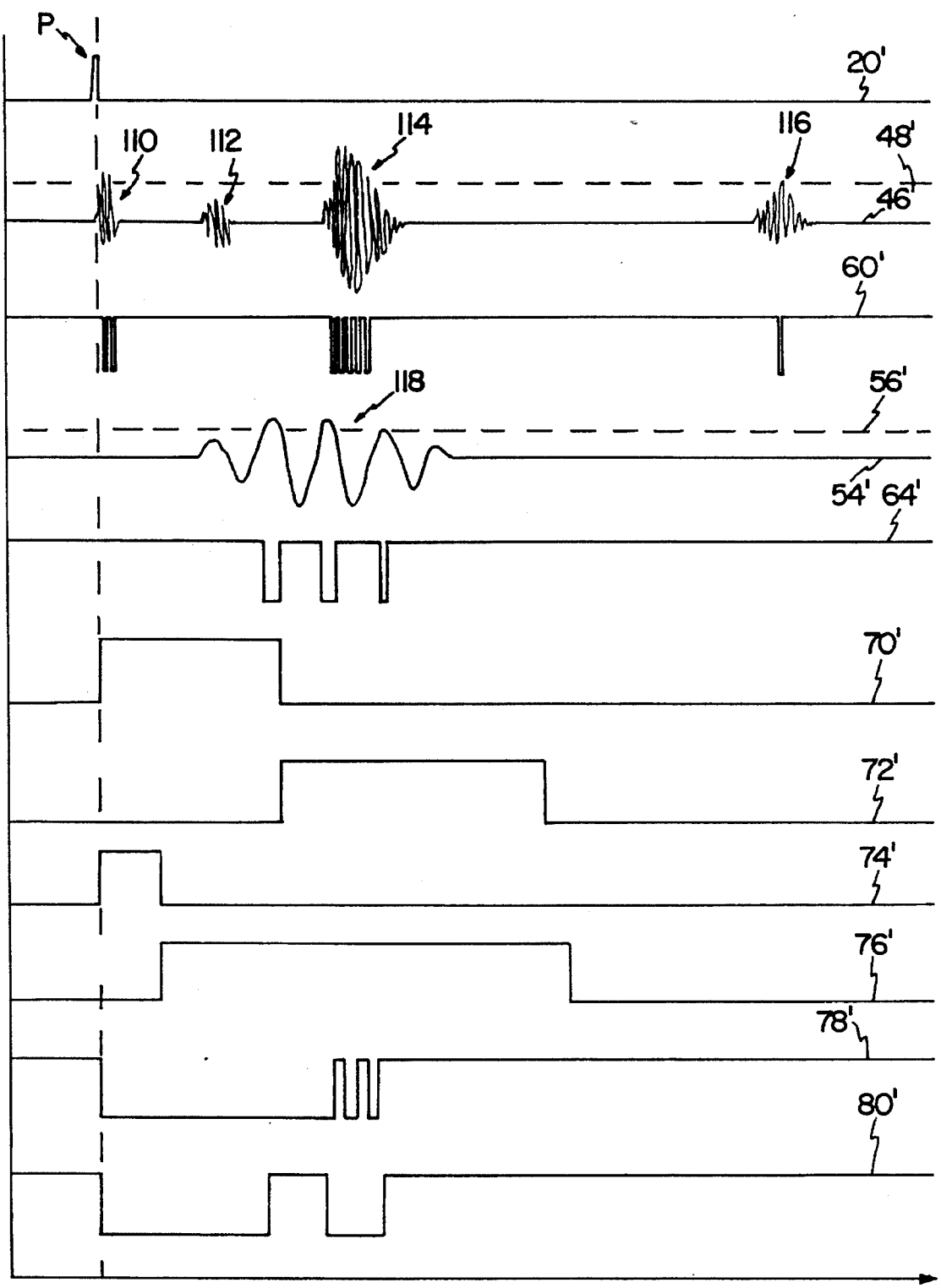
FIG. 3 is a representation of signals obtained at selected points in the circuit shown in FIG. 1 when the material to be sensed is present in the housing gap.

FIG. 2 shows an example of a bandpass filter 102 useable with the invention as either filter 42 or filter 44, depending on the values of the passive circuit components used. In bandpass filter 102, line 104 carries an input signal and line 106 carries a filtered output signal. Numerous other known filters can be used. Preferably, filters 42 and 44, and the remainder of controller 11 circuitry, satisfy intrinsic safety requirements so that controller 11 can be operated in a hazardous environment. FIG. 3 depicts signals at various points in the circuit shown in FIG. 1. The vertical axis represents electric potential (voltage) or electric current, and the horizontal axis represents time. The signals of FIG. 3 are vertically displaced from each other for clarity and ease of comparison, and the reference numeral used for each signal is the same as the numeral used on the corresponding conductor in FIG. 1, except that a prime symbol (') is added to the numeral to distinguish the signal from the conductor. In practical systems, pulse P in signal 20' can cause nearly instantaneous parasitic ringing in signals 46' and 54', shown in signal 46' as wave-train 110. This ringing is due to electromagnetic interference broadcast from the pulse-generating portion of the circuit to other portions of the circuit. Wave-train 112 in signal 46' represents high frequency vibrations 30 propagated through sensor housing 15 and through bridge 32, and detected by receiving crystal 34. Wave-train 112 has been found to be undesirable for use as an indicator of sensor integrity where sensor housing 15 is composed of PFA because the amplitude of wave-train 112 shrinks dramatically at low sensor temperatures (0° C. to −20° C.) compared with moderate to high temperatures (25° C. to +100° C.). Where the sensor housing 15 is composed of metal such as 316 stainless steel, however, little or no such amplitude variations of wave-train 112 with sensor temperature are observed. Wave-train 114 in signal 46' represents high frequency vibrations 30 propagated through the fluid of interest in gap 12 and detected by crystal 34. Where the fluid is absent from gap 12, the amplitude of wave-train 114 is much less than that shown in FIG. 3, well below the level 48' representative of electric potential $V_1$. Wave-trains 112 and 114 are deliberately temporally separated, by the shape of sensor 14 and the materials of construction used for sensor housing 15. In the case of a slot-type sensor mentioned previously, wave-train 112 can occur after wave-train 114 because of the longer path through the sensor housing. Wave-train 116 represents high frequency vibrations propagated multiple times through the fluid of interest in gap 12 as a result of one or more reflections. As with wave-train 114, the amplitude of wave-train 116 decreases significantly when the fluid of interest no longer occupies gap 12.

Signal 60' shows the signal output by comparator 47. Signal 60' makes a transition whenever signal 46' rises above signal 48', and whenever signal 46' dips below signal 48'. Wave-train 118 of signal 54' represents low frequency vibrations 28 propagated through sensor housing 15 and detected by receiving crystal 34. Low frequency wavetrain 118 has been found to be advantageous for use as an indicator of sensor integrity because the amplitude of wave-train 118 remains relatively constant over the entire sensor temperature range, and for different sensor housing materials. The level of signal 56' (i.e., voltage $V_2$) is selected such that the amplitude of wave-train 118 is greater than $V_2$ only when sensor 14 is intact, i.e., when both crystals 26 and 34 are firmly bonded to sensor housing 15 and when sensor housing 15 is undamaged.

In theory, a second low frequency wave-train, resulting from low frequency vibrations propagated across gap 12 and beginning at the time of initiation of corresponding high frequency wave-train 114, can overlap with and distort wave-train 118. However, such a second low frequency wave-train has not been observed in practical systems because, it is believed, of the orientation of transmitting crystal 26 relative to gap 12, and the attachment method of crystal 26 to sensor housing 15. Therefore, temporal overlap of wave-train 118 and wave-train 114 is believed to be acceptable.

Low frequency signal 54' and high frequency signal 46', simultaneously present on line 36 from receiving crystal 34, are effectively isolated from each other by filters 42,44. If desired, video amplifier 38 can be eliminated and, if required, individual amplifiers can be added at the output of each filter 42,44. Other means known to those skilled in the art can also be used, so long as means are provided for isolating the detected high frequency vibrations from the detected low frequency vibrations. High frequency signal 46', after transformation by comparator 47 into signal 60', is gated with time gate signal 72' to yield gated output signal 78'. Pulse P initially sets signal 78' to LO. Thereafter, signal 78' undergoes a transition from HI to LO or from LO to HI whenever signal 60' makes a downward transition (from HI to LO) within the time gate window of signal 72'. Similarly, low frequency signal 54', after transformation by comparator 52 into signal 64', is gated with time gate signal 76' to yield gated output signal 80'. Time gate windows of signals 72',76' are selected to overlap with the features of interest, i.e., wavetrains 114 and 118, respectively, and are preferably slightly wider to make allowance for slight timing variations relative to pulse P due to variations in sensor construction or other variables. The time gate windows, however, are preferably "off" (in a LO state) at all other times so that disturbances from electromagnetic ringing, echoes, and other noise sources do not affect signals 78',80'.

Although the present invention has been described with reference to preferred embodiments, workers skilled in the art will recognize that changes can be made in form and detail without departing from the spirit and scope of the invention. For example, one of the two transducer crystals can be eliminated and the remaining crystal can be used both for generating the ultrasonic vibrations and for generating the electrical transducer signal as a function of received vibrations, with the addition of an ultrasonic vibration reflection member. Also, Digital Signal Processing techniques can substitute for the functions performed by the individual circuit components shown in FIGS. 1 and 2.

What is claimed is:

1. A device for detecting the presence of a fluid at a defined location, comprising:

transducer means for generating vibrations as a function of an electrical drive signal and for generating a transducer output as a function of received vibrations, the transducer means being disposed proximate the defined location such that at least a portion of the transducer output is responsive to the presence of the fluid in the defined location;

an excitation circuit providing the electrical drive signal to induce the vibrations simultaneously at a first and second frequency;

a first and second filter circuit receiving the transducer output and selectively passing the first and second frequencies, respectively, thereby to simultaneously generate first and second filter outputs, respectively; and a control unit coupled to the first and second filter circuits, the control unit indicating the presence of the fluid in the defined location as a function of the first filter output and indicating the integrity of the device as a function of the second filter output.

2. The device of claim 1, further comprising:

a sensor housing carrying the transducer means, the defined location comprising a gap in the sensor housing.

3. The device of claim 2, wherein the sensor housing comprises plastic material.

4. The device of claim 1, wherein the first frequency has a value in the range of 40 KHz to 400 KHz.

5. The device of claim 1, wherein the excitation circuit comprises a pulse generator.

6. The device of claim 1, wherein the first and second filter circuits comprise bandpass filters.

7. The device of claim 1, wherein the first filter comprises a high-pass filter and the second filter comprises a low-pass filter.

8. An ultrasonic sensor for detecting the presence of a fluid at a defined location, comprising:

transducer means for generating vibrations as a function of an electrical drive signal and for generating a transducer output as a function of received vibrations, the transducer output having a first and second frequency component, the transducer means being disposed proximate the defined location such that at least the first frequency component is responsive to the presence of the fluid in the defined location;

a pulse generator coupled to the transducer means and generating the electrical drive signal; and a first and second filter circuit receiving the transducer output and selectively passing the first frequency component and the second frequency component, respectively, thereby to simultaneously generate first and second filter outputs, respectively, the first filter output being responsive to the presence of the fluid in the defined location and the second filter output being responsive to the integrity of the sensor.

9. The sensor of claim 8, further comprising:

a first and second time gate generator to generate first and second time gate signals, respectively;

a first logic circuit receiving the first time gate signal and the first filter output to provide a first sensor output indicative of the presence of the fluid in the defined location; and a second logic circuit receiving the second time gate signal and the second filter output to provide a second sensor output indicative of the integrity of the sensor.

10. A method of detecting the presence of a fluid at a defined location, comprising the steps of:

providing a body having a body portion adjacent the defined location;

initiating vibrations at the body portion simultaneously at a first and second frequency;

detecting the vibrations at the body portion;

filtering the detected vibrations simultaneously through a first and second filter selectively passing the first and second frequency, respectively, to yield a first and second filtered signal, respectively;

providing a first sensor output indicative of the presence of the fluid at the defined location as a function of the first filtered signal; and providing a second sensor output indicative of system integrity as a function of the second filtered signal simultaneously with providing the first filtered output.

11. The method of claim 10, further comprising the steps of:

gating the first filtered signal through a first time gate window to yield a first gated filtered signal; and gating the second filtered signal with a second time gate window to yield a second gated filtered signal;

wherein the providing a first sensor output step is a function of the first gated filtered signal; and wherein the providing a second sensor output step is a function of the second gated filtered signal.

* * * * *

UNITED STATES PATENT AND TRADEMARK OFFICE
CERTIFICATE OF CORRECTION

PATENT NO. : 5,452,611
DATED : September 26, 1995
INVENTOR(S) : Lawrence Jones, Alexander J. Esin and Boris S. Rosselson It is certified that error appears in the above-indentified patent and that said Letters Patent is hereby corrected as shown below:

Col. 2, line 37, please change "pans" to --parts--.

Col. 2, line 47, before the word "Low" please start a new paragraph.

Col. 3, line 38, before the word "Filter 42" please start a new paragraph.

Col. 5, line 15, before the word "FIG. 3" please start a new paragraph.

Col. 5, line 62, please change "wavetrain" to --wave-train--.

Signed and Sealed this

Thirtieth Day of January, 1996

Attest:

BRUCE LEHMAN

*Attesting Officer*   Commissioner of Patents and Trademarks